(12) United States Patent
Merten et al.

(10) Patent No.: US 9,810,607 B2
(45) Date of Patent: Nov. 7, 2017

(54) MICROFLUIDIC DEVICE

(75) Inventors: Christoph Merten, Heidelberg (DE); Ramesh Utharala, Miryalaguda (IN)

(73) Assignee: EMBL, Heidelberg (DE)

( * ) Notice: Subject to any disclaimer, the term of this patent is extended or adjusted under 35 U.S.C. 154(b) by 116 days.

(21) Appl. No.: 14/344,478

(22) PCT Filed: Sep. 14, 2012

(86) PCT No.: PCT/EP2012/068117
§ 371 (c)(1),
(2), (4) Date: May 1, 2014

(87) PCT Pub. No.: WO2013/037962
PCT Pub. Date: Mar. 21, 2013

(65) Prior Publication Data
US 2014/0332083 A1  Nov. 13, 2014

(30) Foreign Application Priority Data

Sep. 14, 2011  (GB) .................................. 1115895.3

(51) Int. Cl.
*G01N 1/28* (2006.01)
*B01L 3/00* (2006.01)
*G01J 3/46* (2006.01)

(52) U.S. Cl.
CPC .......... *G01N 1/28* (2013.01); *B01L 3/502784* (2013.01); *G01J 3/46* (2013.01); *B01L 2200/026* (2013.01); *B01L 2200/061* (2013.01); *B01L 2200/0673* (2013.01); *B01L 2200/0694* (2013.01); *B01L 2300/0816* (2013.01); *B01L 2400/0481* (2013.01); *B01L 2400/0487* (2013.01); *G01J 2003/466* (2013.01);

(Continued)

(58) Field of Classification Search
CPC .... G01N 1/28; B01L 2200/26; B01L 2200/61
See application file for complete search history.

(56) References Cited

U.S. PATENT DOCUMENTS

2003/0201022 A1  10/2003  Kawai
2005/0087122 A1   4/2005  Ismagliov
(Continued)

FOREIGN PATENT DOCUMENTS

DE  102008031798  1/2010
EP       0420296   4/1991
(Continued)

OTHER PUBLICATIONS

Shaojiang Zeng et.al. "Microvalve-actuated precise control of individual droplets in microfluidic devices". Lab on a Chip, vol. 9, No. 10, Jan. 1, 2009, p. 1340.
(Continued)

*Primary Examiner* — Sam P Siefke
(74) *Attorney, Agent, or Firm* — 24IP Law Group; Timothy R DeWitt

(57) ABSTRACT

The present disclosure teaches an apparatus and a method for providing one or more substance liquids to a microfluidic channel network (30). The microfluidic apparatus includes valves for switching the one or more substance liquids to a microfluidic channel network (30). The apparatus can be used to generate a sequence of the one or more substance liquids as individual droplets in an immiscible separation liquid wherein individual ones of the sequence of droplets are located between the separation liquid.

6 Claims, 6 Drawing Sheets

(52) U.S. Cl.
CPC ...... *Y10T 137/0318* (2015.04); *Y10T 137/469* (2015.04); *Y10T 137/877* (2015.04)

(56) References Cited

U.S. PATENT DOCUMENTS

| | | |
|---|---|---|
| 2007/0116594 A1 | 5/2007 | Shimizu |
| 2009/0217742 A1 | 9/2009 | Chiu |
| 2009/0235990 A1 | 9/2009 | Beer |
| 2011/0032513 A1 | 2/2011 | Joanicot |
| 2011/0114190 A1 | 5/2011 | Wen |

FOREIGN PATENT DOCUMENTS

| | | |
|---|---|---|
| EP | 1601874 B1 | 12/2005 |
| EP | 2008716 | 12/2008 |
| EP | 2436444 | 4/2012 |
| GB | 1136779 | 12/1968 |
| JP | 2003190772 | 7/2003 |
| JP | 2009276135 | 11/2009 |
| WO | 2004081741 | 9/2004 |
| WO | 2007081386 | 7/2007 |
| WO | 2007133710 | 11/2007 |
| WO | 2008097559 | 8/2008 |
| WO | 2011090396 | 7/2011 |
| WO | 2011120024 | 9/2011 |

OTHER PUBLICATIONS

"A Microfluidic device for the generation of combinatorial samples".

MICROFLUIDIC DEVICE

The present disclosure relates to a microfluidic apparatus and a method for generating a sequence of substances in a microfluidic channel. The present disclosure relates in particular to a microfluidic apparatus and a method for generating a sequence of encapsulated droplets in a microfluidic channel.

INTRODUCTION AND RELATED ART

Microfluidic devices have shown great potential for many therapeutic, diagnostic, chemical or biochemical applications. They enable work with a minimized amount of substances. One aspect in microfluidics is the control of flows through a channel network. Various techniques have been established to generate and operate microfluidic valves. For example, multilayer soft lithography can be used to fabricate orthogonal channels in two different layers.

Piezo electric acceptors push small pins into the chip made of flexible polymers, thus compressing the channel and stopping the flow within. So far, microfluidic valves have been used mainly to generate small compartments and control the flow in continuous-phase devices. Droplet-based microfluidics systems allow the generation of highly monodisperse (<3% polydispersity in terms of the volume) water-in-oil (w/o) droplets at rates of up to 10,000/s by flow-focusing a continuous aqueous phase with a second immiscible oil phase. Over the last decade, the idea of using these droplets as microreactors for parallelized reactions within a volume range of pico- to nanoliters has been exploited in many different applications. These include nanoparticle synthesis, protein crystallization, single molecule PCR, proteome analysis, clinical diagnosis on human physiological fluids, titration of anticoagulants and the encapsulation and screening of cells. Furthermore, several companies are commercializing droplet-based microfluidics for various applications such as targeted sequencing (e.g. Raindance Technologies, GNUbio) and diagnostics (Droplet Diagnostics).

WO 2007/081386 provides a microfluidic channel for mixing and investigating aqueous phase droplets encapsulated in an oil stream.

A publication of Shaojiang Zeng et al. "Microvalve-actuated precise control of individual droplets in microfluidic devices", LabChip, May 21, 2009; 9(10): 1340-1343 describes an example for the generation of sequences of individual droplets separated by an immiscible oil in a microfluidic channel. A droplet marker is described that is capable of generating four different droplet species that can be fused one by one in a combinatorial fashion. While in theory this approach allows for the generation of many mixtures of different compounds (that can be screened for a desired effect or exploited for on-chip synthesis of compound libraries) the system has several limitations: The system is dependent on droplet fusion and only allows for the generation of combinatorial droplet pairs; The system is driven by negative pressure. All flow is generated by aspirating from the outlet resulting in different droplet sizes for the different compounds when applying constant valve opening times. Even though this can be compensated in theory by adjusting the individual valve opening times, only a poor level of control can be achieved. Since each infused compound needs a specific valve opening time, it seems very challenging to systematically generate all possible droplet pairs (and synchronize the generation of the individual droplets to allow for pairing). In conclusion, the system can be hardly scaled up (the working principle was shown for 4 infused compounds, only, and solely two droplet species were fused). Furthermore, a negative pressure driven system has strict limitations in terms of the maximum flow rates and hence the throughput.

EP 1 601 874 describes the use of mechanical devices such as a Braille-display for closing and opening valves in a microfluidic system.

It is an object of the present disclosure to overcome at least one of the disadvantages of prior art.

SUMMARY OF THE INVENTION

The present disclosure suggests an apparatus and a method for providing a sequence of one or more substance liquids between a separation liquid. The sequence of the one or more substance liquids may be individual droplets in an immiscible separation liquid wherein individual ones of the sequence of droplets are located between the separation liquid. The apparatus comprises a separation liquid channel; a droplet channel; and a substance liquid channel network.

In one aspect the apparatus comprises the substance liquid channel network and the separation liquid channel are connected to the droplet channel through a droplet generation junction, and wherein the substance liquid channel network comprises a first substance liquid inlet, at least one second substance liquid inlet and at least one substance liquid combining area. The use of substance liquid combining area has the advantage that the substance can be brought together in a defined and controlled manner and the substance concentrations of the first substance and at least of the second substance can be controlled. It is also possible to combine or mix more than two substances and the number of substances is only limited by the number of substance inlets ending in the substance liquid combining area. Only one single junction may be used for generating all droplets in the corresponding droplet channel. Droplet fusion is not necessary and can be omitted as the substances are combined prior to droplet formation.

The disclosure also suggests a corresponding method. The method comprises providing a separation liquid to a separation liquid channel, providing at least one of a first substance liquid and at least one second substance liquid to a combination area in the substance liquid channel network to obtain a combined substance liquid, and generating sections of the combined substance liquid separated by the separation liquid in a droplet channel.

The substance liquid combining area may be a section of a microfluidic channel and two or more substance liquids are guides through the combination channel in parallel and/or in sequence. If two or more substance liquids are guide in parallel through the combination channel, they may flow along each other in laminar flow and mixing of the substance may mainly occur during or after droplet generation. However, the combination area may also comprise a mixing section wherein two or more substances are mixed, for example by generating turbulences.

The separation liquid may be, in a water/oil system, an immiscible oil and the substance liquid may be an aqueous solution containing the substance or an organic solvent containing the substance or a combination of an organic solvent and an aqueous solvent. It is also possible to use an organic solvent/water system, wherein the separation liquid is water and the substance liquid is an organic solvent containing the substance. Other systems can be equally used.

In an aspect, the apparatus comprises a separation liquid channel, a droplet channel, and a substance liquid channel network wherein the substance liquid channel network and the separation liquid channel are connected to the droplet channel by a droplet generation junction. The substance liquid channel network comprises at least one first substance liquid inlet, at least one first valve and at least one pressure device for applying a continuous pressure or a continuous flow to the at least one first substance liquid at the at least one first substance liquid inlet. The at least one first valve is switchable between a first position in which a liquid connection to the droplet generation junction is open and a second position in which the liquid connection to the droplet generation junction is closed. Applying a continuous pressure or a continuous flow to the inlet has the advantage that shorter switching times and minimal perturbations occur in the system. In addition, the size distribution of the droplets is more homogeneous and the mixing or combination of substance liquids is better defined and controlled.

The at least one pressure device may be a pump for continuously applying a constant flow or a pressure reservoir for continuously applying a constant pressure. The pressure device can be used for continuously applying the constant flow or constant pressure to a single one of the inlets or to several one or to all inlets in the same time.

The apparatus and the method may further comprise a first substance liquid drain, wherein the substance liquid drain is closed in the first position and wherein the substance liquid drain is open in the second position. Using a drain or waste allows to apply a continuous flow to the inlet and to switch the flow either to the drain or waste or towards the junction. Well controlled and fast switching of the liquids at the junction can be achieved. It is possible to provide an additional drain valve related to the drain. For example the drain valve can be opened to direct a constant flow to the drain when the first valve in the second position. The drain valve may be closed, when the first valve is in the first position.

The disclosure also relates to a corresponding method comprising providing a separation liquid to a separation liquid channel, continuously providing at least a first substance liquid to a first substance liquid channel, and switching at least on first valve directing the first substance liquid to a droplet generation junction, between a first position in which a liquid connection to the droplet generation junction is open and a second position in which the liquid connection to the droplet generation junction is closed.

The present disclosure also suggests a method for providing a coding sequence of droplets, wherein individual ones of the sequence of droplets are located between a separation liquid. The method comprises providing a first substance liquid and at least a second substance liquid to a microfluidic channel and selectively forming droplets of the first substance liquid and of the at least one second substance liquid to generate a predetermined sequence of droplets. In this way, a predetermined sequence of droplets can be generated and used as a coding. The length of the coding is technically unlimited.

Coding can be achieved by using, for example different colors or dyes in the first substance liquid and in the second substance liquid. The dyes can be fluorescent dyes or other dyes that allow distinguishing the droplets containing the first substance from droplets containing the second or any further substance. In this way a two or more color code can be generated.

The coding may be generated in an apparatus and using method as defined above, but the method is not limited to this.

The present disclosure also teaches an apparatus and method for providing one or more substance liquids to a microfluidic channel. The apparatus comprises at least one first substance liquid inlet, at least one first valve and at least one pressure device for continuously applying a constant pressure or a constant flow to the at least one first substance liquid at the at least one first substance liquid inlet, wherein the at least one first valve is switchable between a first position in which a liquid connection to the microfluidic is open and a second position in which the liquid connection to the microfluidic channel is closed. The method comprises continuously providing at least a first substance liquid to a first substance liquid channel, and switching at least one first valve directing the first substance liquid to the microfluidic channel, between a first position in which a liquid connection to the microfluidic channel is open and a second position in which the liquid connection to the droplet generation junction is closed. The method and the apparatus may be used with any type of liquids and fluids.

The apparatus may comprise a first substance liquid drain, and the substance liquid drain may be closed in the first position and may be open in the second position. This ensures that at least one way for the substance liquid is open at any time. A constant flow can thus be applied to the substance liquid inlet allowing short switching times between the inlets.

A person skilled in the art will understand that the above features relating to several aspects of the present disclosure can be combined in any manner.

BRIEF DESCRIPTION OF THE FIGURES

Examples of the present disclosure will now be described with respect to the accompanying Figures in which.

DETAILED DESCRIPTION

The present disclosure may be better understood with respect to examples in which the present invention is implemented. It is to be understood that not all features described with respect to an example have to be implemented and a person skilled in the art will add or remove features to adapt the present disclosure to specific applications or requirements.

Figure 1:
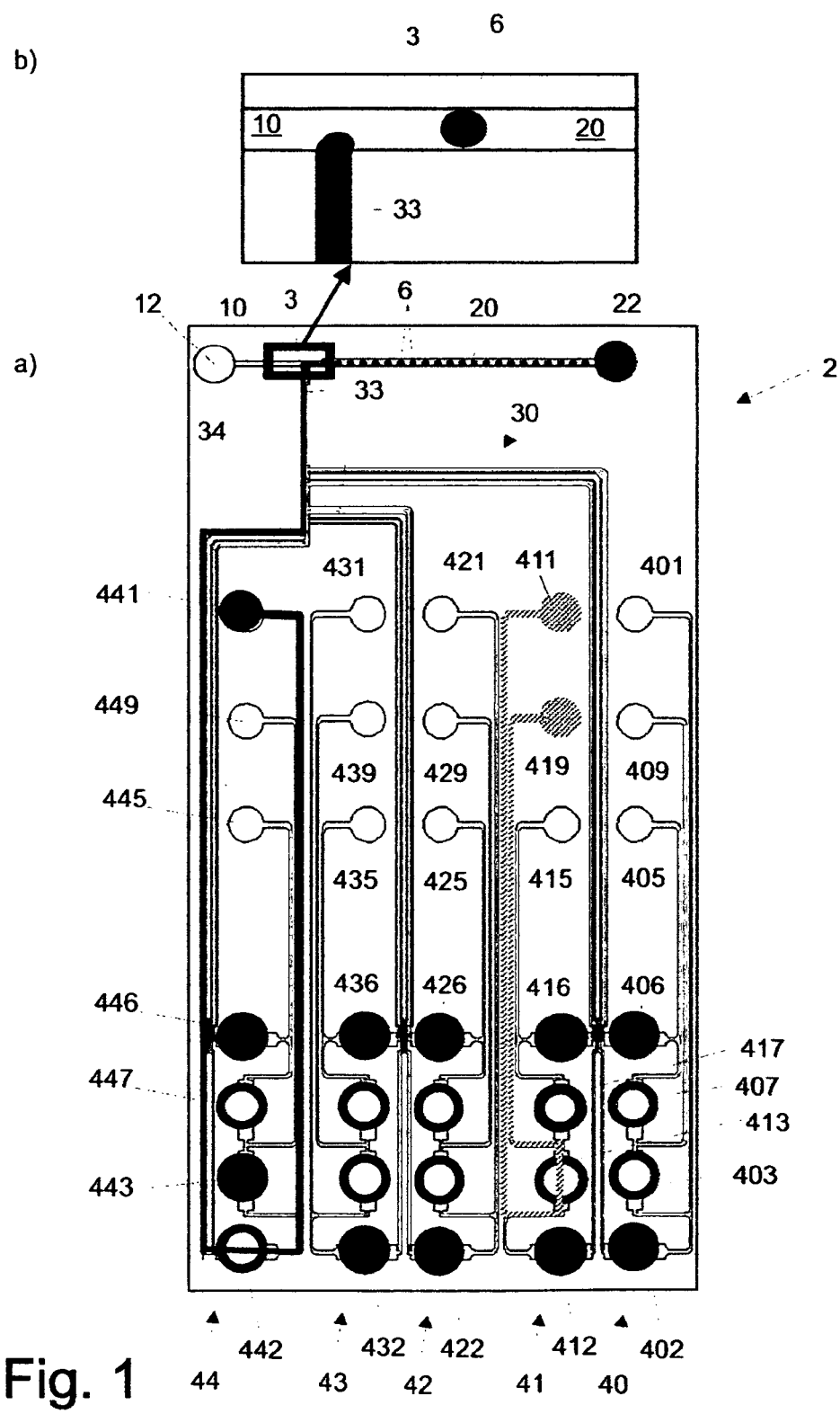
FIGS. 1a and 1b show a general system according to the present disclosure in a first configuration.

FIG. 1 shows an example of a microfluidic channel network 2 in accordance with the present disclosure. FIG. 1a shows the microfluidic channel network 2 comprising separation liquid inlet or oil inlet 12 through which a separation liquid can be inserted into an separation liquid channel 10. The separation liquid may be an immiscible oil, that can be used for encapsulating aqueous droplets as known in the art. The separation liquid channel is termed oil channel 10 with respect to the described example wherein an immiscible fluorinated oil was used as separation liquid. The immiscible oil may be used as separation liquid with aqueous and/or organic solutions as substance liquids. It is, however, also possible to use water or an aqueous solution as separation liquid, for example if the substance liquid is an organic solvent comprising the substance.

In one aspect of the invention, the separation liquid channel 10 has a width of 185 um and a height of 52 μm. Typically the width of the separation liquid channel 10 could vary between 150 μm and 250 μm. The height of the channel will be typically between 40 and 60 μm.

The oil channel 10 is connected to a junction 3 at which droplets are formed, as will be described later. A substance liquid is provided through a combination channel 33 from a substance liquid channel network 30 to the junction 3. The combination channel 33 has a width of 100 μm in this aspect of the invention. More generally the width of the combination channel 33 will be between 80 and 120 μm.

When a substance liquid is provided through the combination channel 33, droplets of the substance liquid are formed at the junction 3 and encapsulated by the separation liquid to form a sequence of droplets separated by the separation liquid. This droplet formation or encapsulation is shown in FIG. 1b in more detail. The junction 3 is connected to a droplet channel 20, which is in the example of FIG. 1 connected to a droplet liquid outlet 22. In the example shown, the junction 3 is a T-junction which has been shown to be reliable for the formation of the droplets. Other types of junction 3 may be used as well. The substance liquid may be an aqueous solution that may contain one or more substances in different concentrations. The substance liquid is prepared and in some cases combined in the substance liquid channel network as will be described in more detail below.

The droplet channel 20 may comprise an investigation area (not shown) or may comprise further features (branches/valves) for investigating or separating the droplets generated in the droplet channel 20. The droplets are generated by encapsulating droplets of an aqueous liquid generated in the substance liquid channel network 30. The substance channel network 30 is combined or connected to the droplet channel 20 via the combination or mixing channel 33. By providing a constant and/or continuous flow of oil in the oil liquid channel 10 and of at least one aqueous substance liquid in the combination channel 33 the droplets of the aqueous substance liquid provided in the combination channel 33 will be encapsulated between sections of the oil separation liquid into the droplets that will be moved along the droplet channel 20.

The T-junction 3 is the only connection of the substance liquid channel network 30 and the all of the droplets are formed from the aqueous liquid provided in the combination channel 33.

While a T-junction 3 is used in the described examples, the present disclosure is not ii to this type of junction, and other types of junctions may be equally used. For example a flow focusing junction can be used as described for example in "Vyawahare S, Griffiths A D, Merten C A. Miniaturization and parallelization of biological and chemical assays in microfluidic devices. *Chem Biol*. Oct. 29, 2010; 17(10):1052-1065" the content of which is incorporated by reference herewith.

Figure 2:
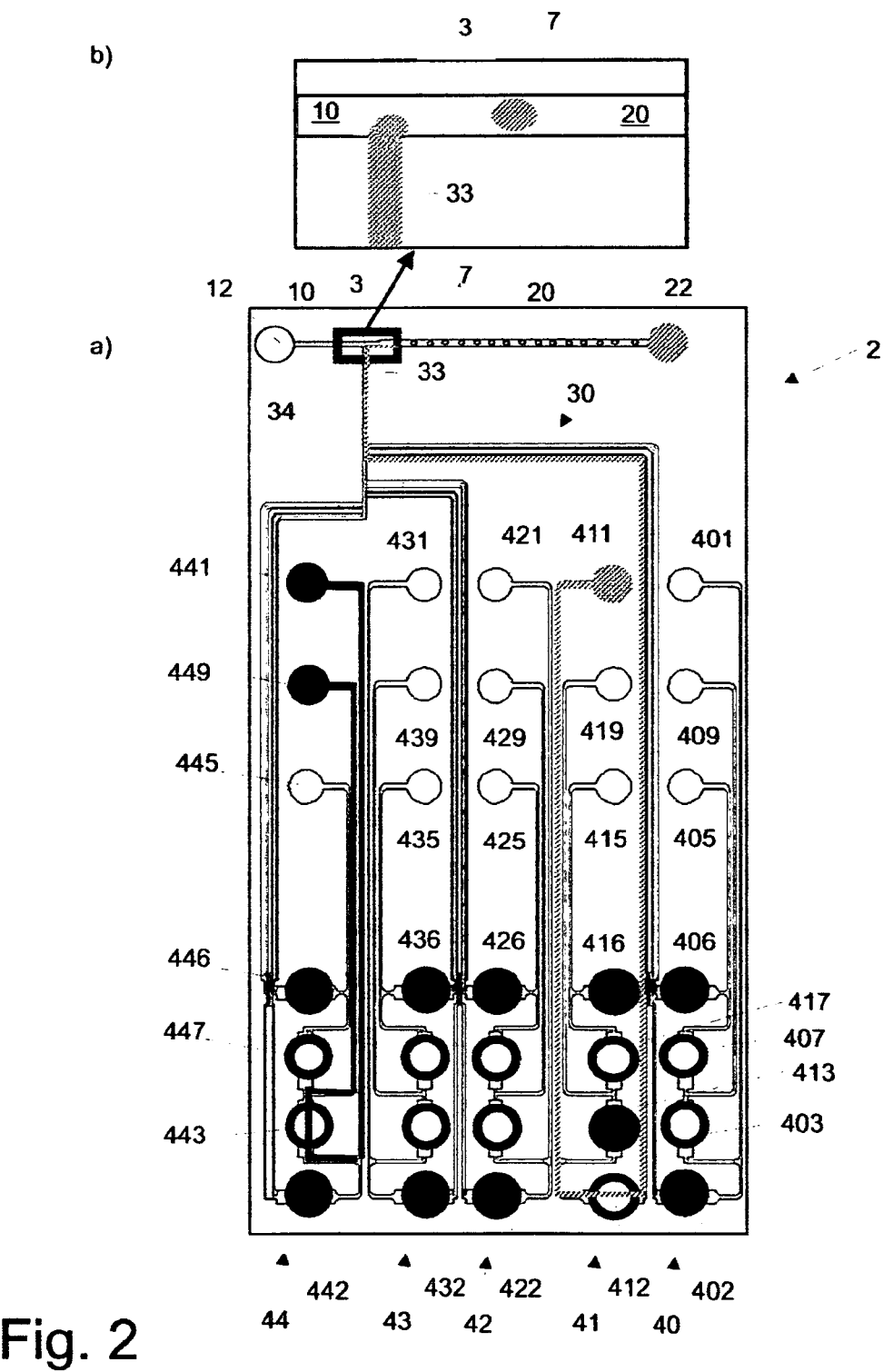
FIGS. 2a and 2b show the microfluidic channel system of FIG. 1 in a second configuration.

The combination channel 33 is the connection between the substance liquid channel network 30 and the separation channel 10. The combination channel 33 is connected to a plurality of inlet areas 40, 41, 42, 43, 44. The substance liquid channel network 30 is shown in FIGS. 1 and 2 with five inlet areas for illustrative purposes, but the invention is not limited to this number. It is equally possible to provide less or more than the shown five inlet areas 40, 41, 42, 43, 44. Each of the inlet areas 40, 41, 42, 43, 44 comprises two inlets and a waste outlet. All inlet areas 40, 41, 42, 43, 44 have a similar design which will now be described in more detail with respect to the first inlet area 41 and the fourth inlet area 44 illustrated in two different configurations in FIG. 1, and FIG. 2. FIGS. 1 and 2 show the same apparatus 2 in a different configuration, i.e. with different valves activated.

A first inlet 411 of the first inlet area is connected to an inlet channel which leads to a first inlet or distribution valve 412 and to a first waste valve 413. The first inlet valve 412 and the first waste valve 413 may be activated alternatively. In the configuration shown in FIG. 1, the first inlet valve 412 is closed and the first waste valve 413 is open. A liquid containing a first substance is inserted through the first inlet 411 and the liquid is guided via the open waste valve 413 to the first waste outlet 419. The waste outlet 419 may be connected to a waste container and a fresh liquid containing a first substance is continuously introduced through the first inlet 411.

In one aspect of the disclosure, the inlet channel will have a width of around 50 μm and more generally between 40 and 60 μm. The valves are 490 μm and more generally between 440 and 550 μm. The height of the channel is 52 μm and more generally between 40 and 60 μm.

It is also possible to connect the waste outlet 419 to a reservoir and to reuse the substance liquid from the reservoir. The first substance liquid may be continuously circulated.

While the first inlet valve 412 is closed in the configuration of FIG. 1, a fourth substance liquid inserted to a fourth inlet 441 is guided to the combination area 34 and the combination channel 22 for forming and encapsulating the droplets from the fourth substance liquid provided the fourth inlet 441 of the fourth inlet area 44. In a similar configuration to the first inlet area 41, the fourth substance liquid provided through the fourth inlet 441 is guided to a fourth inlet valve 442 and a fourth waste valve 443. In the configuration illustrated in FIG. 1 the fourth inlet valve 443 is open and the fourth waste valve is close. The fourth substance liquid entered at the fourth inlet 441 is guided to the combination area 34 and via the combination channel 33 to the T-junction 3. The fourth liquid is formed into the droplets 6 in the droplet channel 20 as also shown FIG. 1b.

FIG. 2 shows a different configuration. The fourth inlet valve 442 is now closed and the corresponding waste valve 443 is open. The fourth liquid from the fourth liquid inlet 441 will be guided to the fourth waste 449. A continuous flow of liquid can be maintained through fourth inlet 441. In contrast, the first inlet valve 412 is now open in the configuration of FIG. 2 and the first waste valve 413 is closed for the first substance liquid provided at the first inlet 411. The first substance liquid is now guided to the combination area 34 and to the combination channel 33 and droplets from the first substance liquid 7 are formed in the droplet channel 20 as illustrated in FIG. 2.

One simple application of the microfluidic apparatus 2 is described with respect FIGS. 1 and 2 referring to two substance liquids, a first substance liquid provided at first inlet 411 and the fourth substance liquid provided at the fourth inlet 441. It is to be understood that at least a second substance liquid and a third substance liquid can be provided to the second substance liquid inlet 421 and the third substance liquid inlet 431 and to substance liquid inlet 401. These inlets are designed in the same way and it is possible to encapsulate at least all of the four substance liquids in the channel network illustrated in FIG. 2 in this way.

In addition to the first substance inlet 411, to the second substance liquid inlet 421, the third substance liquid inlet 431 and fourth substance liquid inlet 441 and the substance liquid inlet 401, each of the inlet networks 40, 41, 42, 43, 44 comprises an additional inlet 405, 415, 425, 435, 445. Each one of the additional inlets 405, 415, 425, 435, 445 comprises a pair of an additional inlet valve 406, 416, 426, 436, 446 and an additional waste valve 407, 417, 427, 437, 447. For example, the first additional inlet 415 of the first inlet area 41 comprises an additional first inlet valve 416 and an additional first waste valve 417. By adding this additional inlets and additional valves it is possible to use in total eight different substances at eight different substance liquid inlets to the microfluidic apparatus shown in the example of FIGS. 1, 2 and 3.

In the example shown, the additional inlets 405, 415, 425, 435, 445 are connected via the corresponding additional waste valve 407, 417, 427, 437, 447 to the waste outlet 409, 419, 429, 439, 449 of the corresponding inlet are 40, 41, 42, 43, 44, respectively. One waste outlet is used for two inlets. It is, however, also possible to provide a separate waste outlet for each waste valve, i.e. for each inlet, for example, if the corresponding substance liquids shall be reused. It is also possible to combine more than two inlets to a common waste outlet.

Figure 3:
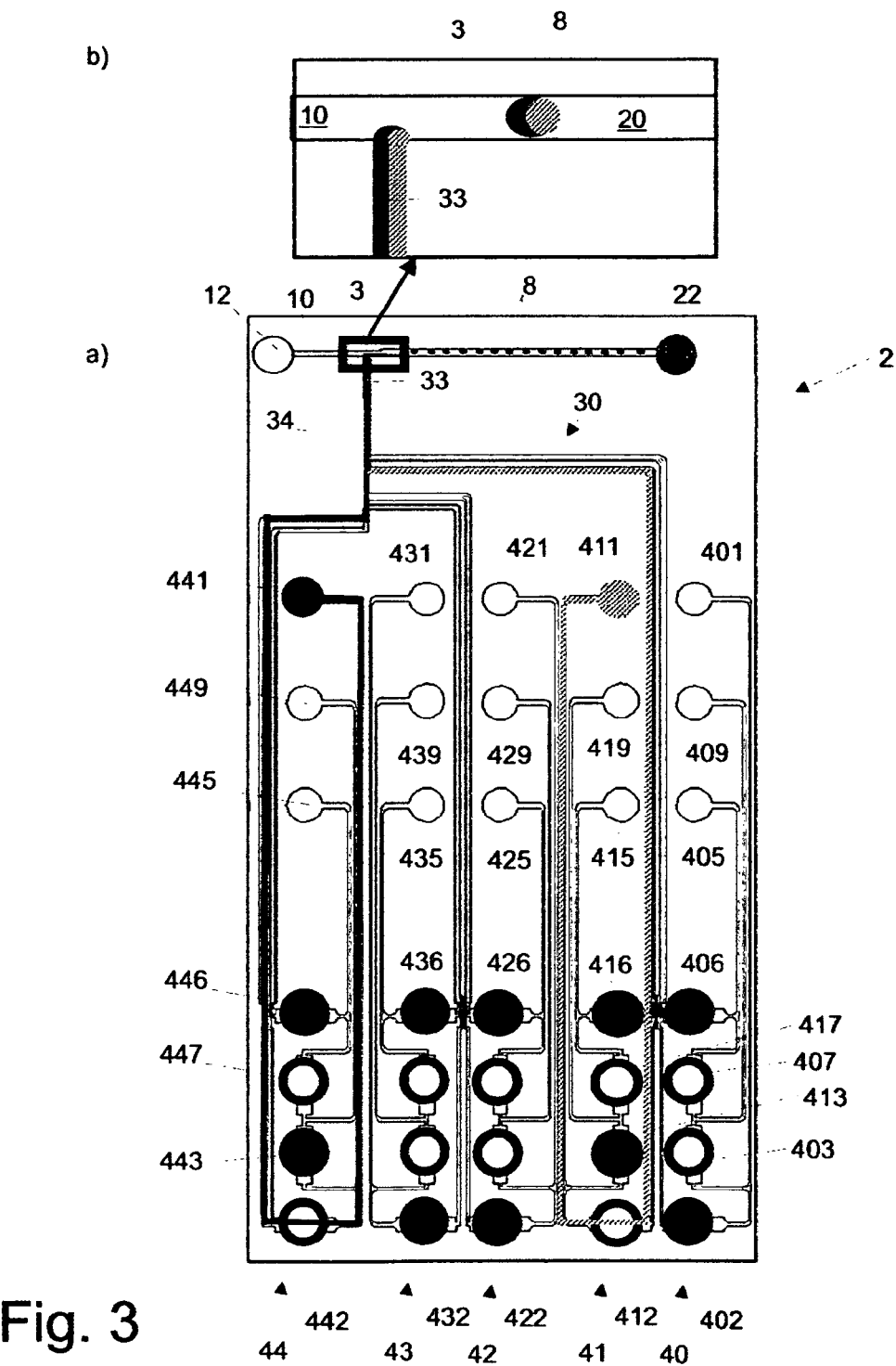
FIGS. 3a and 3b show the microfluidic channel system of FIGS. 1 and 2 in a third configuration

All of the inlets are arranged in the substance liquid channel network and are combined in the combination or mixing area 34 into a single combination channel 33. In this way droplets of eight different substances can be encapsulated with this example. It is possible to use each of the eight substances separately. It is also possible to combine two or more substances in a droplet by opening two or more of the inlet valves 402, 406, 412, 416, 422, 426, 432, 436, 442, 446 at the same time, as shown in FIG. 3. In the example of FIG. 3, the first inlet valve 412 and the fourth inlet valve 442 are open, while all other inlet valves are closed and the substance liquid introduced at first inlet 411 and at the fourth inlet 441 are combined in the combination area 34 and transferred to the T-junction 3 via combination channel 33. A sequence of combined droplets 8 containing the first substance and the second substance can be generated.

Figure 4:
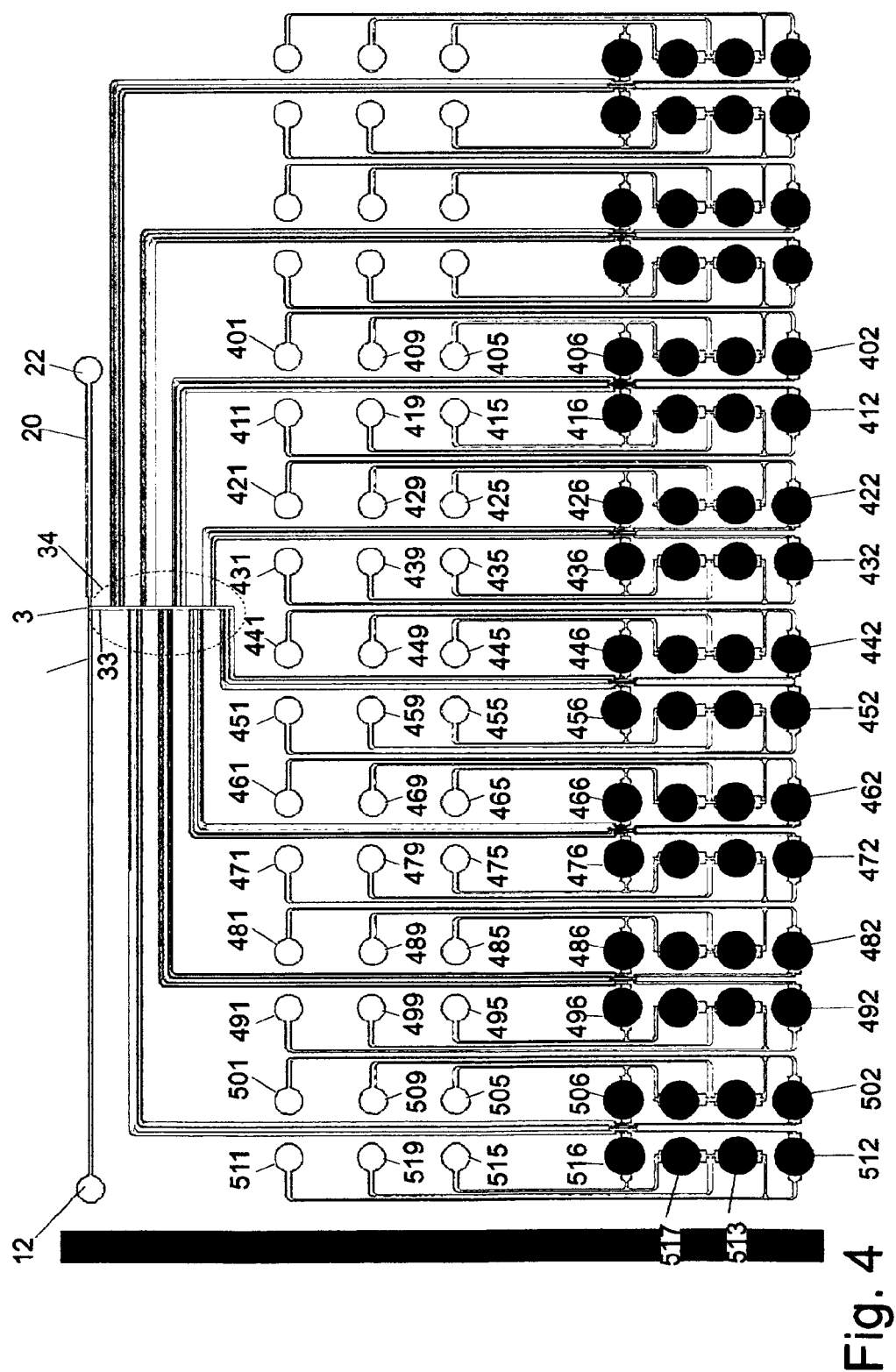
FIG. 4 shows a second example of a microfluidic channel system of the present disclosure.

The examples of FIGS. 1, 2 and 3 have been described with respect to four and eight substance channel inlets. It is obvious to a person skilled in the art that the disclosure is not limited to this number. Many more inlets with an inlet and waste valve arrangement shown in FIGS. 1, 2 and 3 can be used and combined in a single mixing area 34. An example is illustrated in FIG. 4. The example of FIG. 4 shows in total sixteen substance inlet networks each with an inlet channel and an additional inlet channel allowing in this example the addition of thirty-two substance liquids that can be combined into a sequence of droplets via the single T-junction 3. The sequence or droplets may thus contain up to 32 different droplets and all their combinations in this example. In the example shown in FIG. 4, all valves are in closed state which may be an initial state. It is obvious, that each of the valves, can be individually opened to allow liquids to pass to the junction 3 or to a waste as explained with the examples of FIGS. 1 to 3.

It is possible to generate an unlimited number of sequence combinations. Some of these sequence combinations can be used for example for coding or for screening high number of compounds using "coding droplets". The sequence combinations can be used as a type of "bar code" to indicate a position within the separation liquid. This enables, for example, an identification of the product droplets 7 in the separation channel 10. For example, some of the droplets 7 can be used for analysis (as described below) and other droplets form the identification (bar code) so that an experimenter is able to identify the product droplets 7 of interest.

It will be appreciated that different coding schemes can be used. For example single digits can be coded with one colour and tens with a further colour. In this coding scheme the number "25" would be coded as two droplets of a first colour followed by five droplets of a second colour. Alternatively a binary scheme could be used in which the first colour represented a 1 and the second colour represented a 0. In this coding scheme sample 10 (=2) would be one colour droplet followed by the second colour droplet and binary 101 (=5 decimal) would be a first colour droplet followed by the second colour droplet and finally the first colour droplet again.

The number of droplets can also be determined by the "length" of a droplet plug in the channel. For example, rather than generating separate droplets the length of the plug is determined by the time in which the dye is inserted into the separation channel 10 and can be read out optically. So, for example, each one of the first colour or the second colour can be injected for 500 ms into the separation channel 10 and the length of the droplet plug formed into the separation channel 10 measured.

In one aspect of the disclosure, the substance liquids making up the identification code are inserted into the separation channel 10 at one or more different junctions 3 at which the coding droplets are formed. This is because dyes or fluorophores that are used to form the identification code may interfere with reactions in the product droplets 7 of interest. Two different junctions 3 are used so that each unction 3 is used for one single dye.

In one aspect of the invention the substance liquids for the identification code are food dyes.

The generation of sequences is performed by activating the corresponding inlet valves. The inlet valves and the waste valves may use a Braille display for activating the valves. A pin of the Braille display may be aligned with a corresponding valve and the valve can be closed by pressing the pin onto the valve to compress the channel. Braille displays may be preferred as they provide fast switching times of about 500 ms or less. Other valves known in the art of microfluidics may be used as well.

The substance liquids are continuously supplied to the respective inlets, for example by pumps. The speed of the pumps or the pressure provided does not need to be changed. Changing of the substance liquid is solely performed by switching the corresponding valves. This pressure driven system ensures a homogeneous droplet size.

The examples have been described in a manner that at any point in time only one inlet valve is open at a time allowing the passage of only one substance liquid into the droplet channel. However, it is also possible to open two or more valves at the same time. This will lead to a mixing of the substance liquids provided through the corresponding inlets. This can be used to combine and mix different substances provided at the different inlets in a predefined manner.

It is also possible to use this concept for dilution of a substance and to perform different types of assays or investigations with the disclosed system.

EXAMPLES

Example 1: Stem Cell Differentiation

The microfluidic apparatus 2 is used to screen media ingredients (e.g. growth factors and chemical stimuli) triggering the differentiation of stem cells into specific lineages (e.g. neurons, muscle cells, etc.). It is well known that the differentiation of stem cells is dependent on many (chemical) factors in parallel. Hence screening combinatorial mixtures of media ingredients is required and even commercially exploited in conventional systems (e.g. plasticell). While a conventional setup requires large amounts of stem cells and only allows for relatively low throughput, the microfluidic apparatus 2 of the present disclosure can circumvent these limitations.

In this example, a suspension of stem cells as well as a number of growth factors and chemical stimuli are continuously injected into (different inlets of) the microfluidic apparatus 2. Using a predefined sequence of valve configurations, all possible combinations of growth factors and chemical stimuli are co-encapsulated together with the stem cells into droplets. Downstream of the encapsulation step, the droplets 6 are incubated for a time period sufficient to allow for differentiation of the stem cells into different lineages.

Subsequently, the droplets 6 are mixed with assay reagents (e.g. antibodies) to identify the resulting cell lineages. For this purpose, the droplets 6 containing the stem cells are fused with droplets containing the assay reagents before an on-chip fluorescence readout or an imaging step is performed to visualize binding of specific antibodies (indicating the differentiation into a specific lineage).

Even though all sample compositions are generated in a predefined sequence and the order of the resulting droplets is kept constant throughout the whole experiment, additional barcoding of the samples might be desired in order to enable accurate determination of the droplets 6. This can be achieved by injecting specific fluorophores into particular aqueous inlets and directing their flow towards the drop maker each time after changing the valve configurations, hence generating droplets forming the identification code and showing a specific fluorescence signal. By using two different fluorophores, injecting them in an alternating fashion and varying the number of generated droplets (or just the concentration of the fluorophores) sample numbers can be written in form of optical barcodes shown in FIGS. 5a and b.

Figure 5A:
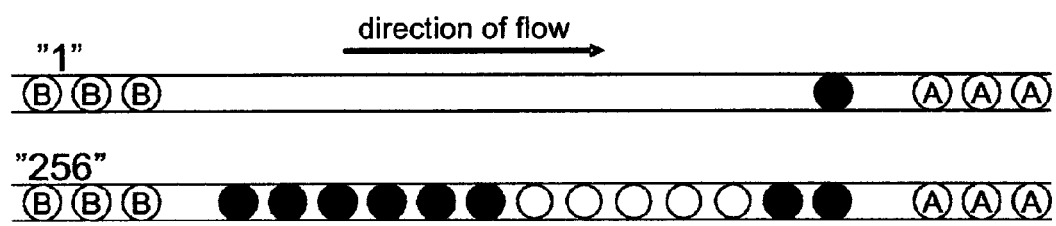
FIGS. 5a and 5b show possible segments of encapsulated liquid droplets that may be generated with the microfluidic apparatus.

Methodology 1: Generation of optical barcodes (large numbers) in between the combinatorial samples (indicated by letters) using 2 fluorophores injected and encapsulated in an alternating fashion (changing the fluorophore indicates the next digit) while varying the number of generated droplets. An example is shown in FIG. 5a.

Figure 5B:
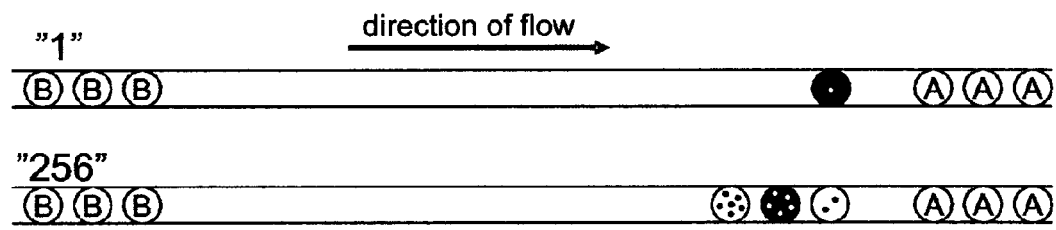

Methodology 2: Generation of optical barcodes (large numbers) in between the combinatorial samples (indicated by letters) using two different fluorophores injected and encapsulated in an alternating fashion (changing the fluorophore indicates the next digit) while using ten different concentrations of each fluorophore. An example is shown in FIG. 5b.

Example 2: Combinatorial Chemistry

The novel microfluidic apparatus 2 is used to set up samples containing different reactants for the combinatorial synthesis of bioactive molecules. For example, the microfluidic apparatus 2 can be used to mix azides and alkenes for "click chemistry" reactions (e.g. Huisgen 1,3-Dipolar Cycloaddition) in a combinatorial fashion. In this approach, a number of alkenes (n) and a number of azides (z) are continuously injected into the microfluidic apparatus 2. Using a predefined sequence of valve configurations, all possible alkeneazide pairs are co-encapsulated into the product droplets 6. Downstream of the encapsulation step, the product droplets 6 are incubated at elevated temperature for a time period sufficient to obtain the products of the chemical reactions.

Subsequently, the product droplets 6 are mixed with assay reagents to test for biological activity of the newly generated products. For this purpose, the product droplets 6 are fused with droplets containing all assay reagents (e.g. a drug target and a fluorogenic substrate allowing to monitor its activity) before an on-chip fluorescence readout is performed. The product droplets 6 combined with the assay reagents showing a specific fluorescence signal (e.g. particularly high/low fluorescence intensities) indicate potent inhibition of the drug target by a newly synthesized compound.

Even though all sample compositions are generated in a predefined sequence and the order of the resulting droplets is kept constant throughout the whole experiment, additional barcoding of the samples using coding droplets might be desired and can be achieved as described in example 1.

Example 3: Screening Potent Drug Combinations

Many diseases cannot be cured based on the application of a single drug acting on a single drug target. For example, HIV infections are usually treated using highly active antiretroviral therapy (HAART). In this approach, drug cocktails targeting different viral proteins (e.g. Reverse Transcriptase, HIV protease or the Envelope protein) are administered at the same time to avoid the generation of resistant mutants. Similarly, the treatment of cancer or multi-resistant bacteria often involves the application of drug cocktails.

The microfluidic apparatus 2 of the present disclosure can be used to systematically encapsulate all possible combinations of a given number of drugs into droplets and monitor their potentially cumulative effects on a co-encapsulated pathogen (also infused through one of the inlets of the device). After the sample generation and an incubation time allowing the pathogen to proliferate, the product droplets 7 and their contents are mixed with assay reagents for a viability read-out. For this purpose, the product droplets 7 are fused with reagent droplets containing all assay reagents (e.g. coupling the viability of the pathogen with a fluorescence signal) before an on-chip fluorescence readout is performed. The fused droplets showing a specific fluorescence signal (e.g. particularly high/low fluorescence intensities) indicate efficient killing of the pathogen by a specific drug cocktail.

Optional barcoding of the samples might be desired and can be achieved as described in example 1.

Example 4: Studying Cellular Pathways Using Chemical Perturbations

The microfluidic apparatus 2 of the present disclosure is used to analyze and map cellular pathways and/or interactions of different cellular factors (e.g. proteins). For this purpose, the pathways are perturbed using combinations of known inhibitory or stimulating compounds (in regard to a certain phenotype). Subsequently a readout is performed to analyze if the combination of compounds results in cumulative, saturated or competitive effects (compared to the effect of individual compounds). For example, if the combination of two inhibitors does not mediate stronger inhibition than each of the two inhibitors individually, it seems highly likely that their targets are involved in the same pathway. In contrast, in case a cumulative (increased) effect is observed, it is more likely that the targets are involved in two different pathways that are not directly linked. Systematic screening of combinations of inhibitors and stimuli hence allows to derive detailed interaction maps of cellular pathways.

The microfluidic apparatus 2 of the present disclosure can be used to systematically encapsulate all possible combinations of a set of different inhibitors and stimuli into droplets and monitor their effects on co-encapsulated cells (also infused through one of the inlets of the device). After their generation, the samples in the product droplets 7 are incubated to allow for inhibition or stimulation of their corresponding cellular targets. Subsequently, the contents of the product droplets 7 are mixed with assay reagents allowing to monitor the phenotype. For example, the product droplets 7 are fused with reagent droplets containing all assay reagents (e.g. coupling the inhibition of cellular pathways with a fluorescence signal) before an on-chip fluorescence readout is performed. Quantitative readout of the fluorescence signals allows determination if the combination of compounds results in cumulative, saturated or competitive effects and hence enables to derive a detailed interaction map (regarding the targets of the compounds).

Optional barcoding of the samples might be desired and can be achieved as described in example 1.

It is apparent to a person skilled in the art that it is not necessary to implement all features of the present disclosure. For example it is possible to provide only one or two inlets. It is also possible to provide a plurality of T-junctions connected to a plurality of substance liquid channel networks.

Example 5: Combinatorial Mixtures

Figure 6A:
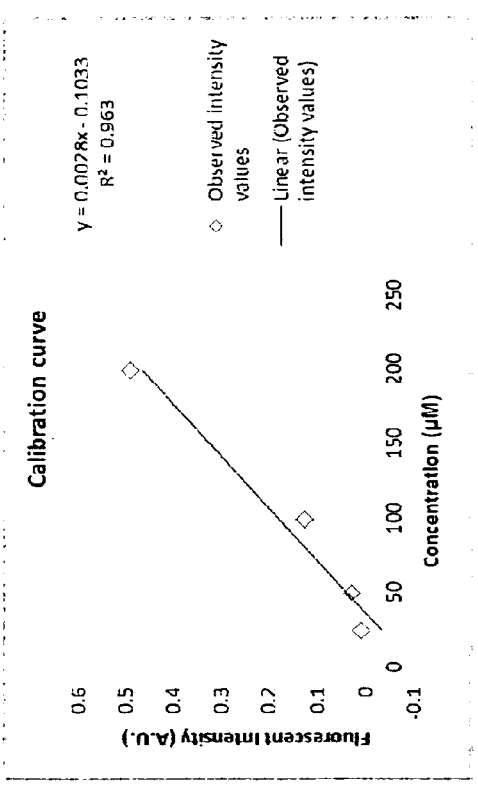
FIGS. 6a-c show an example of combinatorial mixtures using the microfluidic apparatus.
Figure 6C:
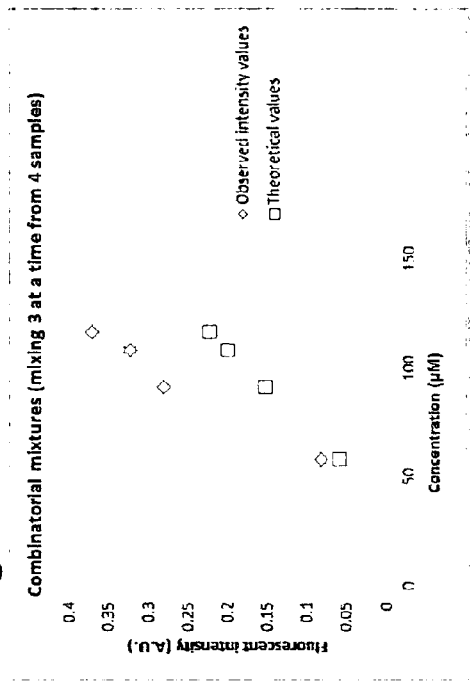
Figure 6B:
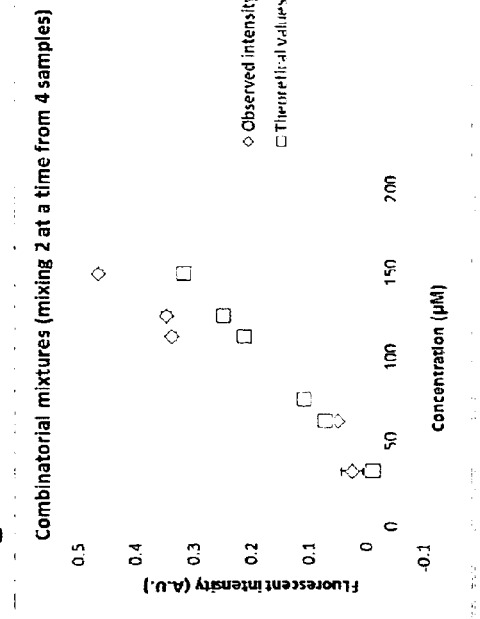

The microfluidic apparatus of the disclosure can be used to generate combinatorial mixtures. An example is shown in FIG. 6a-c in which four different concentrations of a fluorescent dye are used as the substance liquids. FIG. 6a shows on the x-axis the concentrations of the dye (25 µm, 50 µm, 100 µm and 200 µm) and on the y-axis the degree of fluorescence in arbitrary units (AU). A regression line was fitted to the data and was best represented by the equation $y=0.0028x-0.1033$.

FIG. 6b shows the result of mixing various combinations of two of the concentrations of the dye in approximately equal amounts. The squares show the theoretical values calculated from the equation and the rhombi show the actual measured results. Similarly FIG. 6c shows the results of mixing three of the concentrations of the die in approximately equal amounts. The experimental results are substantially in agreement with the theoretical results calculated. This shows that combinatorial mixing can take place in the microfluidic channel network 30.

Example 6: Combination with Microscope

It is further possible to combine the droplet channel 20 with a microscope or other investigation or experimental setups to investigate the compounds generated in the droplet sequence. The droplet sequence may also be used for further experiments and may be applied to biological and non-biological systems arranged inside the micro channel network.

The invention claimed is:

1. A microfluidic apparatus for providing one or more substance liquids to a microfluidic channel network, the microfluidic apparatus comprising the microfluidic channel network, at least one first substance liquid inlet, a second substance liquid inlet, at least one first inlet valve, a second inlet valve, and at least one input device for continuously applying a substantially constant pressure or a substantially continuous flow to the at least one first substance liquid at the at least one first substance liquid inlet,
wherein the microfluidic channel network comprises a substance liquid combining area, the substance liquid combining area being connected to a droplet generation junction, and wherein the at least one first inlet valve is switchable between a first position, in which a liquid connection from the at least one first substance liquid inlet to the substance liquid combining area-is open, and a second position, in which the liquid connection from the at least one first substance liquid inlet to substance liquid combining area-is closed,
wherein the second inlet valve is switchable between a first position in which a liquid connection from the second substance liquid inlet to the substance liquid combing area microfluidic channel network is open, and a second position, in which the liquid connection from the second substance liquid inlet to substance liquid combining area the microfluidic channel network is closed.

2. The microfluidic apparatus of claim 1, further comprising a first substance liquid drain fluidly connectable to the first substance inlet, wherein the substance liquid drain is closed in a first position and wherein the substance liquid drain is open in a second position.

3. The microfluidic apparatus according to claim 1, further comprising:
a separation liquid channel; and
a droplet channel;
wherein the separation liquid channel is connected to the droplet channel at the droplet generation junction.

4. The microfluidic apparatus of claim 3, further comprising a substance liquid combining area which is a section of a microfluidic channel.

5. The microfluidic apparatus of claim 3, wherein at least one of the separation liquid channel and the droplet channel are, in use, filled with a separation liquid of an immiscible oil.

6. The microfluidic apparatus according to claim 1, wherein the first substance liquid is at least one of an aqueous solution, an organic solvent or a combination thereof comprising a first substance.

* * * * *